United States Patent
Fan (10) Patent No.: US 9,155,881 B2
(45) Date of Patent: Oct. 13, 2015

(54) NON-PLANAR CHIP ASSEMBLY

(75) Inventor: Long-Sheng Fan, Hsinchu (TW)

(73) Assignee: IRIDIUM MEDICAL TECHNOLOGY CO, LTD., Hsinchu (TW)

( * ) Notice: Subject to any disclaimer, the term of this patent is extended or adjusted under 35 U.S.C. 154(b) by 97 days.

(21) Appl. No.: 13/300,548

(22) Filed: Nov. 18, 2011

(65) Prior Publication Data

US 2012/0283799 A1 Nov. 8, 2012

Related U.S. Application Data

(63) Continuation-in-part of application No. 13/282,423, filed on Oct. 26, 2011, which is a continuation-in-part of application No. 13/102,596, filed on May 6, 2011, now abandoned.

(60) Provisional application No. 61/553,919, filed on Oct. 31, 2011.

(51) Int. Cl.
*A61N 1/00* (2006.01)
*A61N 1/05* (2006.01)
*A61N 1/08* (2006.01)
*A61N 1/375* (2006.01)
*A61N 1/36* (2006.01)
*H01L 27/146* (2006.01)

(52) U.S. Cl.
CPC .............. *A61N 1/0543* (2013.01); *A61N 1/08* (2013.01); *A61N 1/36046* (2013.01); *A61N 1/375* (2013.01); *H01L 27/14618* (2013.01)

(58) Field of Classification Search
CPC . A61N 1/0543; A61N 1/36046; A61N 1/375; A61N 1/08; H01L 27/14618
USPC .......................................... 607/2, 53, 54, 141
See application file for complete search history.

(56) References Cited

U.S. PATENT DOCUMENTS 5,476,494 A  12/1995  Edell et al.
5,650,363 A   7/1997  Endroes et al.
(Continued)

FOREIGN PATENT DOCUMENTS

JP   07283365    10/1995
JP   2003318218  11/2003
JP   2006-051164  2/2006

OTHER PUBLICATIONS

Ng, David C. et al., "Impantable Microimagers," Sensors 2008, 8(5), 3183-3204, May 15, 2008.
(Continued)

*Primary Examiner* — Niketa Patel
*Assistant Examiner* — Lindsey G Hankins
(74) *Attorney, Agent, or Firm* — Blakely Sokoloff Taylor & Zafman LLP (57) ABSTRACT

A non-planner integrated circuit device comprising a flexible structure and at least one fixture structure bonded to the flexible structure is described. The flexible structure may be curved in a desired deformation. A plurality of contact areas may be included in the flexible structure. Circuitry may be embedded within the flexible structure to perform processing operations. In one embodiment, the fixture structure may be bonded with the fixture structure via the contact areas to provide holding constraints allowing the flexible structure to remain curved. The bonding pads can also be used to connect communications in electrical signals.

22 Claims, 12 Drawing Sheets

(56) References Cited

U.S. PATENT DOCUMENTS

| | | | |
|---|---|---|---|
| 5,840,199 A | | 11/1998 | Warren |
| 6,068,632 A | | 5/2000 | Carchidi et al. |
| 6,150,676 A | | 11/2000 | Sasaki |
| 6,294,831 B1 | | 9/2001 | Shishido et al. |
| 6,324,429 B1 | | 11/2001 | Shire et al. |
| 6,392,143 B1 | | 5/2002 | Koshio |
| 7,035,692 B1 | | 4/2006 | Maghribi et al. |
| 7,079,900 B2 | | 7/2006 | Greenburg et al. |
| 7,091,619 B2 | | 8/2006 | Aoyagi |
| 7,113,661 B2 | | 9/2006 | Arai et al. |
| 7,127,301 B1 | * | 10/2006 | Okandan et al. ............. 607/116 |
| 7,130,693 B1 | | 10/2006 | Montalbo |
| 7,158,836 B2 | | 1/2007 | Suzuki |
| 7,840,274 B2 | | 11/2010 | Greenberg et al. |
| 7,914,842 B1 | | 3/2011 | Greenberg et al. |
| 8,142,190 B2 | | 3/2012 | Anitua Aldecoa |
| 8,150,526 B2 | | 4/2012 | Gross et al. |
| 8,209,023 B2 | | 6/2012 | Zhou et al. |
| 8,322,027 B1 | | 12/2012 | Greenberg et al. |
| 2002/0091422 A1 | | 7/2002 | Greenberg et al. |
| 2002/0094508 A1 | | 7/2002 | Lorenzi |
| 2002/0099420 A1 | | 7/2002 | Chow et al. |
| 2002/0111655 A1 | | 8/2002 | Scribner |
| 2003/0114904 A1 | | 6/2003 | Ovadia et al. |
| 2003/0160303 A1 | | 8/2003 | Hirokawa et al. |
| 2003/0209792 A1 | | 11/2003 | Takaishi |
| 2005/0082684 A1 | | 4/2005 | Aiba et al. |
| 2005/0161818 A1 | | 7/2005 | Basceri |
| 2006/0184245 A1 | | 8/2006 | Graf et al. |
| 2006/0241753 A1 | | 10/2006 | Suaning et al. |
| 2006/0273304 A1 | | 12/2006 | Cok |
| 2007/0142877 A1 | | 6/2007 | McLean |
| 2007/0257373 A1 | | 11/2007 | Akram et al. |
| 2008/0058897 A1 | | 3/2008 | McMahon et al. |
| 2008/0065208 A1 | * | 3/2008 | Greenberg et al. ........... 623/6.63 |
| 2008/0086206 A1 | | 4/2008 | Nasiatka et al. |
| 2008/0288067 A1 | * | 11/2008 | Flood ........................... 623/6.63 |
| 2008/0294224 A1 | | 11/2008 | Greenberg et al. |
| 2009/0264972 A1 | | 10/2009 | Zhou et al. |
| 2009/0326594 A1 | * | 12/2009 | North et al. ........................ 607/2 |
| 2010/0184285 A1 | | 7/2010 | Hua et al. |
| 2010/0204754 A1 | | 8/2010 | Gross et al. |
| 2010/0298895 A1 | | 11/2010 | Ghaffari et al. |
| 2011/0108180 A1 | * | 5/2011 | Fendler et al. .................. 156/50 |
| 2011/0172736 A1 | | 7/2011 | Gefen et al. |
| 2011/0307042 A1 | | 12/2011 | DeCarmine |

OTHER PUBLICATIONS

Tokuda, Takashi et al., "Flexible and extendible neural interface device based on cooperative multi-chip CMOS LSI architecture," Sensors and Actuators A 122 (2005), 88-98, May 25, 2005.

International Search Report and Written Opinion mailed Jul. 6, 2012, for International Patent Application No. PCT/US2011/064014, 18 pages.

Fan, L.-S. et al., "Monolithically Integrated Flexible Artificial Retina Microsystems Technology and in vitro Characterization," Association for Research in Vision and Ophthalmology, ARVO 2010, May 2-6, 2010, Ft. Lauderdale, Florida, USA, abstract.

Fan, Long-Sheng et al., "A Flexible & Translucent CMOS Retinal Prosthesis and in vitro Characterization," Association for Research in Vision and Ophthalmology, ARVO 2011, May 15, 2011, Ft. Lauderdale, Florida, USA, abstract.

Fan, L.-S. et al., "A Flexible Sensing CMOS Technology for Sensor-Integrated, Intelligent Retinal Prosthesis," Asia-Pacific Conference on Vision, APCV 2010, Jul. 23-26, 2010, Taipei, Taiwan, abstract.

Zrenner, Eberhart et al., "Subretinal electronic chips allow blind patients to read letters and combine them to words," Proceedings of the Royal Society B, 2011, 278, 1489-1497, downloaded from http://rspb.royalsocietypublishing.org/, Jul. 18, 2011.

Shire, Douglas B. et al., "Development and Implantation of a Minimally Invasive Wireless Subretinal Neurostimulator," IEEE Transactions on Biomedical Engineering, vol. 56, No. 10, Oct. 2009.

Ahuja, A. K., et al., "Blind subjects implanted with the Argus II retinal prosthesis are able to improve performance in a spatial-motor task," British Journal of Ophthalmology, 95:539-543, Sep. 29, 2010, downloaded from http://bjo.bmj.com/, Jul. 28, 2011.

International Search Report and Written Opinion mailed Apr. 25, 2012, for International Patent Application No. PCT/US2011/058159, 20 pages.

The Association for Research in Vision and Ophtalmology, Late Breaking Abstracts, for Sight: The Future of Eye and Vision Research, May 2-6, 2010.

Chichilnisky, et al., "Functional Asymmetries in on and Off Ganglion Cells of Primate Retina", *The Journal of Neuroscience*, 22(7), (Apr. 1, 2002), pp. 2737-2747.

Graf, "Bendable Electronics for Retinal Implants", *Ultra-thin Chip Technology and Applications*, Chapter 28, Springer New York, (Nov. 12, 2010), pp. 363-375.

\* cited by examiner

NON-PLANAR CHIP ASSEMBLY

CLAIM TO PRIORITY

The present application is a continuation in part application of U.S. patent application Ser. No. 13/282,423 filed on Oct. 26, 2011, which is a continuation in part application of U.S. patent application Ser. No. 13/102,596 filed on May 6, 2011. The present application also claims the benefit of Provisional Patent Application No. 61/553,919, filed on Oct. 31, 2011. These applications are hereby incorporated by reference in their entirety into this application.

FIELD OF INVENTION

The present invention relates generally to micro devices, and more particularly to assembly of three-dimensional curved flexible device chips.

BACKGROUND

Integrated electronic circuit (IC) industry relies on "planar" technology to reduce the limit of feature size of photolithography and to progress according to Moore's law, since the depth of focus is reduced when the numerical aperture is increased to define finer features in photolithography. However, planar surfaces of devices based on such planar technologies may limit geometry of interactions and/or interconnections among these devices or with an external system or external systems.

Thus, traditional planar technologies may not be capable of providing devices with non-planar geometries to minimize complexity of interactions among the devices or with external systems.

SUMMARY OF THE DESCRIPTION

In one embodiment, an assembly method for non-planar (e.g. quasi-spherical) structures, such as non-planar surface patch of a semiconductor chip (or chip stack) may comprise depositing stressed films on either side (or both sides) of a thin semiconductor substrate of a thin chip for small deformations of the chip.

In another embodiment, stressed films may be deposited with patterning of the stressed films (for example, by using photolithography and etching or lift-off process) for small deformations with controlled shapes.

In another embodiment, slots may be created on thin chips and stressed films may be deposited to allow large deformation of the chip.

In another embodiment, slots may be created on thin chips and the chips may be bonded to a separate piece of a constraining element (for example, a ring-shaped patch or another chip) to allow larger deformation of the chips. The bonding may be mechanically constraining to provide electrical connections between bonded pieces of elements (including the chips).

In another embodiment, a combination of slots with stressed films and constraining elements can form a curved surface for the chips.

In another embodiment, two or more slotted pieces of the chips may be bonded to have mutual or multiple constraints to hold curved pieces in place.

In some embodiments, curved structures thus formed may be suitable for brain-machine interfaces (such as retinal prosthesis), or new architectures of 3D interconnections of processing units.

An embodiment of the present invention includes a non-planner integrated circuit device comprising a flexible structure and at least one fixture structure bonded to the flexible structure. The flexible structure may be curved in a desired deformation. A plurality of contact areas may be included in the flexible structure. Circuitry may be embedded within the flexible structure to perform processing operations. In one embodiment, the fixture structure may be bonded with the fixture structure via the contact areas to provide holding constraints allowing the flexible structure to remain curved.

In another embodiment, a three dimensional integrated circuit device with a three dimensional shaped surface may comprise a plurality of flexible chips and a plurality of bonding. Each flexible chip may be curved conforming to the three dimensional shaped surface. At least two of the flexible chips may be configured to face each other without obstruction inside the device. The flexible chips may be bonded together via the bonding pads. Each flexible chip may be bonded with at least a separate one of the flexible chips via two or more of the bonding pads to provide mutual holding constraints to allow the bonded flexible chips to remain curved. In one embodiment, the device may comprise connection paths between the flexible chips facing each other to allow direct communication between the flexible chips facing each other. The bonding pads and the connection paths may provide connection configuration among the flexible chips to perform processing operations.

In yet another embodiment, an implant flexible device may comprise a plurality of photo sensors to receive light, a plurality of micro electrodes and circuitry coupled to the photo sensors and the micro electrodes. The circuitry may drive the micro electrodes to stimulate neuron cells for enabling perception of a vision of the light captured by the photo sensors. The device may be made of a flexible material having slots to form openings in the material. The slots may allow the device to be curved in a desired deformation conforming to a shape of a human eyeball to enable positioning the micro electrodes in close proximity to the neuron cells for the stimulation.

Other features of the present invention will be apparent from the accompanying drawings and from the detailed description that follows.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Retina chip assembly processes or non-planar (such as quasi-spherical) surface patches of (integrated) semiconductor chips and methods are described herein. In the following description, numerous specific details are set forth to provide thorough explanation of embodiments of the present invention. It will be apparent, however, to one skilled in the art, that embodiments of the present invention may be practiced without these specific details. In other instances, well-known components, structures, and techniques have not been shown in detail in order not to obscure the understanding of this description.

Reference in the specification to "one embodiment" or "an embodiment" means that a particular feature, structure, or characteristic described in connection with the embodiment can be included in at least one embodiment of the invention. The appearances of the phrase "in one embodiment" in various places in the specification do not necessarily all refer to the same embodiment.

In one embodiment, it is advantageous to have non-planar surfaces of integrated active devices, transistor circuits, transducers or micro systems, to change the geometry of interactions, interconnections among these devices, sub-systems, or interactions, interconnections with an external system, or external systems. Integrated devices with non-planar shapes or geometries may enable new computational architectures (such as a ball-shaped geometry is a "round-table forum" in 3D optimizing the interactions, communications, and interconnections between computational elements on the surfaces, and communication/interaction link inside the sphere). It enables new ways of interfacing electronics or photonics to biological neural systems in general (such as in the brain-machine interface (BMI), quasi-spherical surfaces are frequently encountered).

For example, in the case of an artificial retina, the interface between the prosthesis device and the retina at the back of a human eyeball is a quasi-spherical surface with a radius of curvature of ~12.5 mm. To minimize the complexity of interconnections through eyeballs, it is desirable to collocate the interfacing micro electrodes and electronic circuitry, and together in close proximity to the surface of retina neurons. This disclosure teaches the method to form the typically rigid semiconductor electronics into the non-planar (here, quasi-spherical) shape.

FIGS. 1A-1D are schematic diagrams illustrating exemplary embodiments of non-planar assembly for flexible chips. Assembly 100A of FIG. 1A may illustrate an artificial retinal prosthesis device in a quasi-spherical shape conforming to the shape of the retina in an eyeball to allow the device positioned in close proximity to the surface of retina neurons. The conformity of the shape thus may reduce the required electrical excitation thresholds of neurons and increases the granularity of the interface between the device (e.g. via electrodes) and the retina neurons.

Figure 1A:
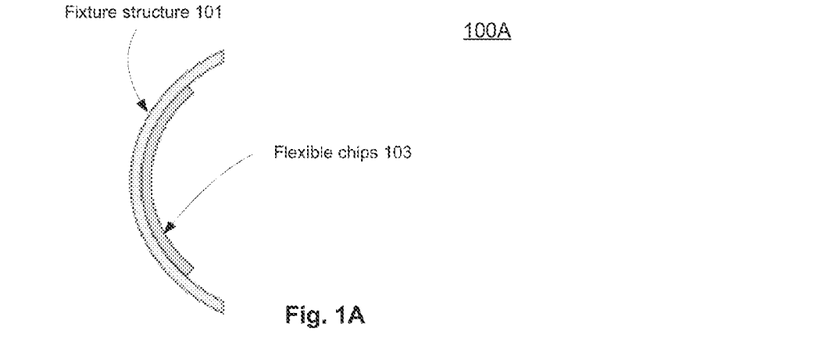
FIGS. 1A-1D are schematic diagrams illustrating exemplary embodiments of non-planar assembly for flexible chips.

In one embodiment, assembly 100A may comprise flexible chips 103 with light sensors, electrodes, driving circuits, etc. Flexible chips 103 may be mechanically constrained to be curved in a desired shape or deformation via fixture structure 101. For example, fixture structure 101 may comprise a flexible polymer material shaped or deformed with a desired curvature. Flexible chips 103 may be bonded or fixed to fixture structure 101 to remain curved in the desired shape.

Figure 1B:
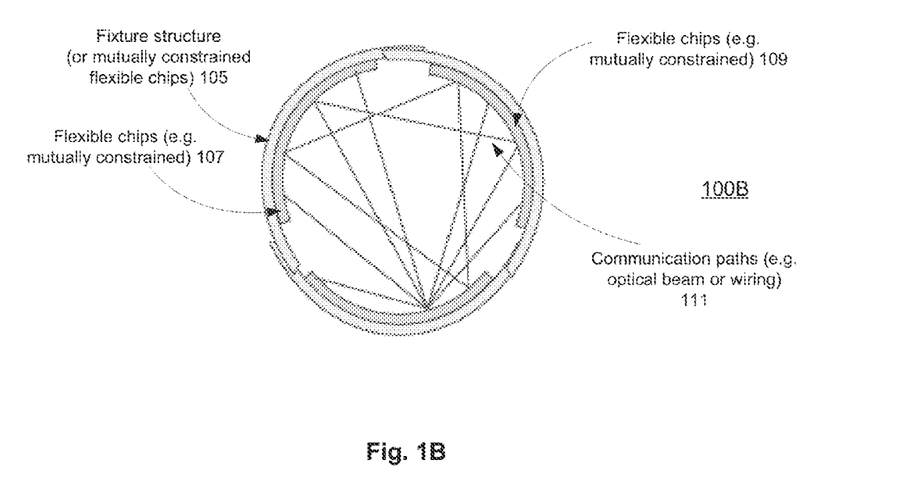

Turning now to FIG. 1B, assembly 100B may be a relatively spherical-shaped assembly comprising multi-layers of flexible chips. For example, flexible chips 107, 109 may be deformed to facilitate communications among surface elements of the chips 107, 109. Chips 107, 109 may be positioned or configured to face each other to establish communication paths, such as communication path 111, using either optical beams, wirings or other applicable connections. In some embodiments, a communication path between different curved chips facing in the same direction (such as ships 105, 107) may be based on through-silicon via. The through silicon via may bring some pads of a thin IC chip through its thin silicon substrate to the backside (e.g. from front side) of the thin IC chip so multiple chips can be stacked and bonded together. Multiple chips, such as fixture structure 105, flexible chips 107, may remain curved in assembly 100B based on mutual constraints between these chips.

The non-planar geometry of assembly 100B may enable computational architectures based on connections or other applicable non-planner shaped features. For example, a ball-shaped geometry in a sphere assembly may be a "round-table forum" in 3D (three dimensional) geometry for optimizing the interactions, communications, and interconnections between computational elements (or circuitry of flexible chips) on the surfaces of the sphere assembly, and communication/interaction links for elements located inside the sphere assembly.

Figure 1C:
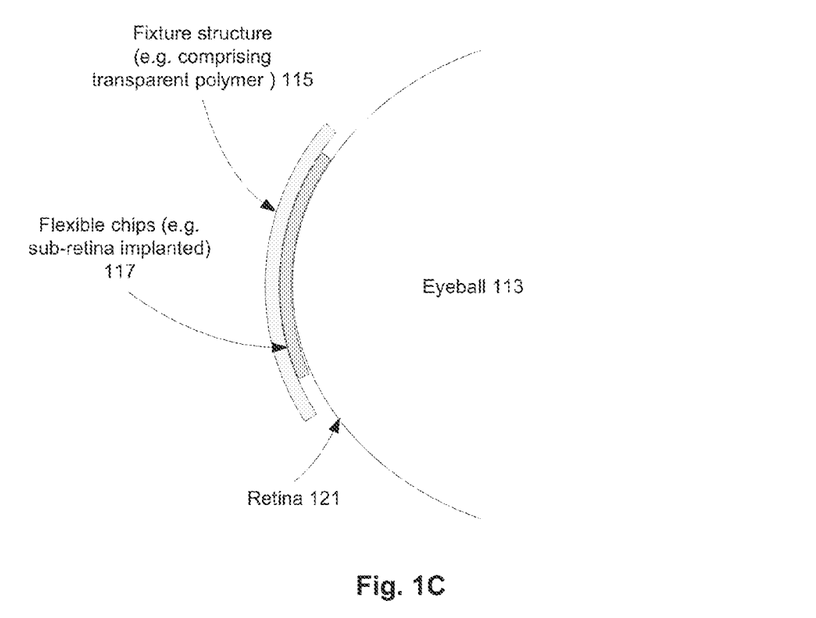

Turning now to FIG. 1C, a non-planar artificial retina assembly may be implanted for eyeball 113 in a sub-retina manner. The artificial retina may include flexible chips 117 in close contact with retina 121 of eyeball 113. Flexible chips 117 may be bonded with fixture structure 115 to remain curved to conform to the shape of eyeball 113. In one embodiment, both fixture structure 115 and flexible chips 117 may comprise transparent material to allow light to pass through.

Figure 1D:
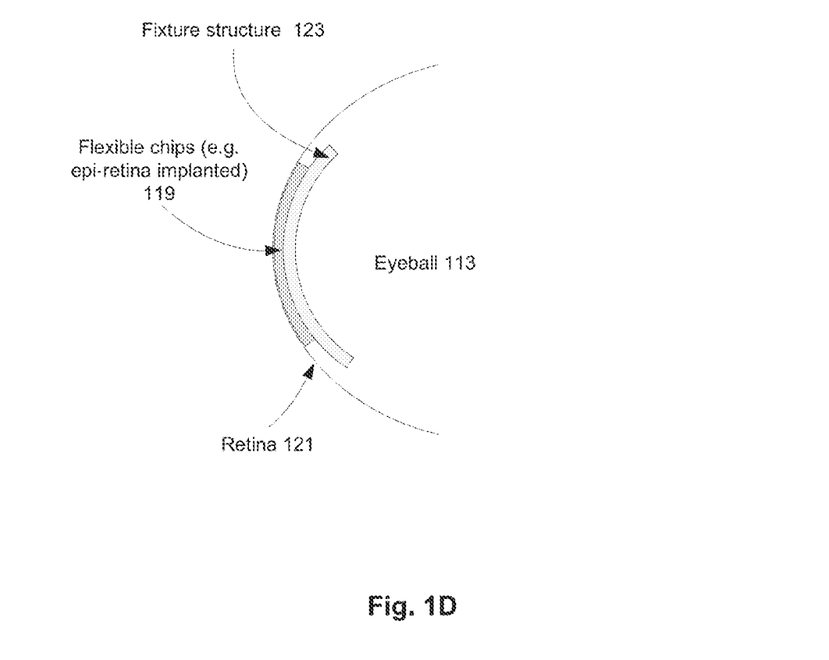

Alternatively, in FIG. 1D, a non-planar artificial retina assembly may be implanted for eyeball 113 in an epi-retina manner. The artificial retina may include flexible chips 119 in close contact with retina 121 from inside of eyeball 113. In addition, the artificial retina may include fixture structure 123 to provide mechanical constraints to allow flexible chips 119 to remain curved conforming to the shape of eyeball 113. The non-planar artificial retina assembly may be flexible so as to be deformed according to various configurations or shapes desired.

Figure 2A:
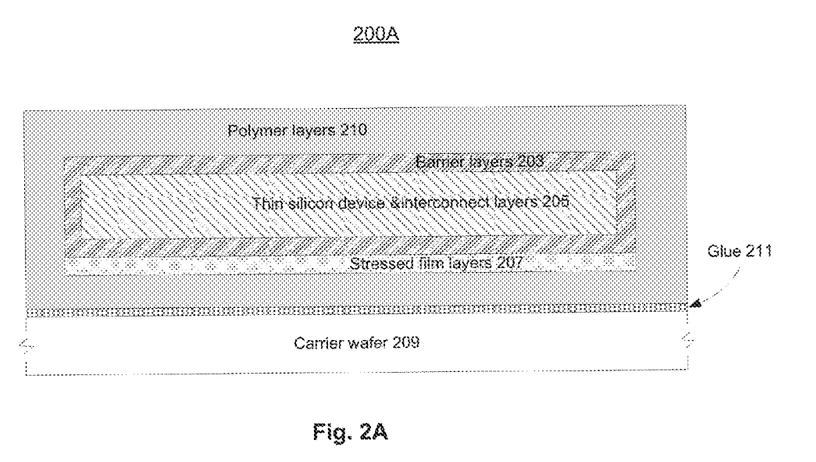
FIG. 2A is a block diagram illustrating cross sectional views of a flexible structure deposited with a stressed thin film according to embodiments described herein.

FIG. 2A is a block diagram illustrating cross sectional views of a flexible structure (or device) deposited with a stressed thin film. In one embodiment, structure 200 may include thin device layers 205 sandwiched between barrier layers 203 and polymers 210. Device layers 205 may be based on a thin MOS (Metal Oxide Semiconductor) die intended for medical implant wrapped by barrier layers 203 and biocompatible polymer layers 210 to protect against device corrosion and/or poisoning living tissues. Structure 200A may be thin enough to curl (or bend, deform) according to stress or stretching force from stressed film layers 207.

In some embodiments, stressed thin films, such as stressed film layers 207, may be deposited in either side or both sides of a thin structure or chip to achieve desired deformation (e.g. with a certain degrees bending) for the chip. For example, stressed thin films may be pre-compressed or pre-stretched to apply bending force in different directions. Optionally, stressed thin films can be patterned (for example, in annular shapes or long stripes by photolithography and etching processes) during the fabrication process to create various curved shapes (e.g. in a wavy manner or other applicable forms) for the thin structure. Structure 200 may curl when released from thick carrier wafer (or handle wafer) 209 attached via glue 211.

Figure 2B:
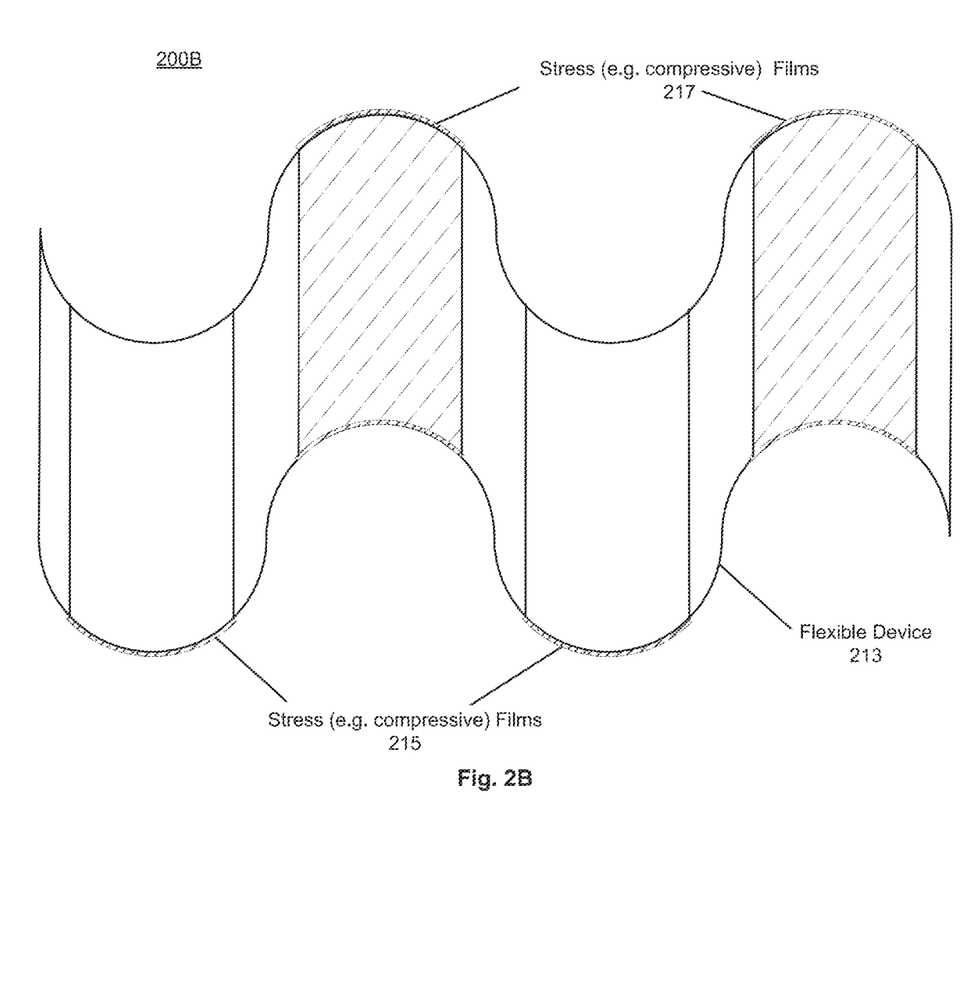
FIG. 2B is a schematic diagram illustrating a non-planar device deformed in a wavy manner according to embodiments described herein.

FIG. 2B is a schematic diagram illustrating a non-planar device deformed in a wavy manner according to embodiments described herein. For example, non-planner integrated circuit device 200B may include a flexible thin structure 213 curved in a wavy manner. Stressed films 215, 217 may be formed (e.g. via pattern masks) on both sides of structure 213 to form a specific (or pre-designated) pattern (e.g. stripes, zigzag, or other applicable patterns etc.) to curve structure 213 in a desired deformation, such as a wavy manner. In one embodiment, stress film 215 may be pre-compressed or compressive. Alternatively, stress films may be pre-stretched. Stress films 215,127 may provide displacement constraints or force, such as large residual thin film stresses, to curve the flexible structure 213 in the desired deformation. A non-planar device may include a combination of pre-compressed, pre-stretched, or compressive films formed in a designated pattern to provide stress distributions according the designated pattern to achieve desired deformation of the device.

According to one embodiment, desired deformation may include chip bending curvature. For example, if flexible chips are to be deformed into a non-planar spherical patch from a planar disk, the required reduction in the circumference of the outer circle of the flexible chips can be calculated. In one embodiment, estimation of the chip bending curvature caused by deposited thin films with residual film stresses (on a relatively thick substrate) may be based on "Stoney Equation" (or approximation equation) when the displacement from the substrate bending is much less than the wafer thickness (e.g. thickness of device layers 205). For larger stresses on thin chips, numerical methods may be used to calculate the chip bending curvature without over-estimating the displacement via the approximation equation, as the displacement can easily be larger than the substrate thickness due to two-dimensional constraints.

Figure 3A:
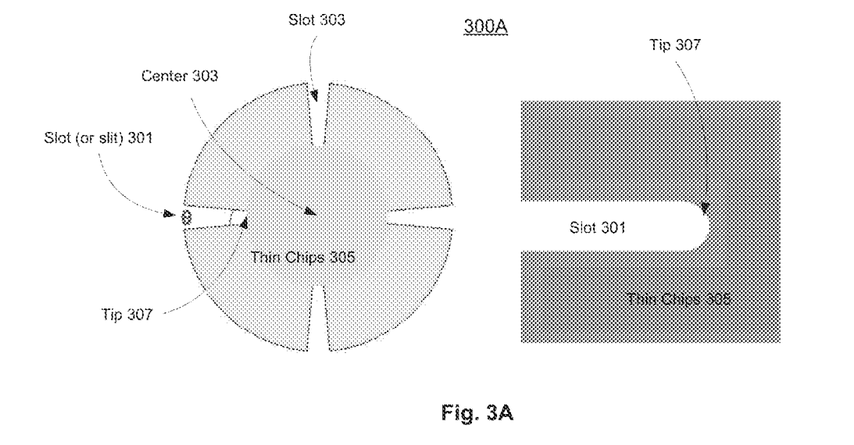
FIGS. 3A-3C are schematic diagrams illustrating exemplary non-planar chips based on slots according to embodiments described herein.
Figure 3B:
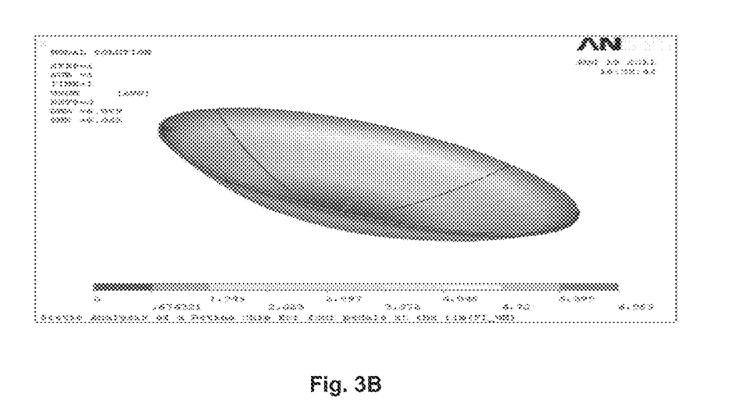
Figure 3C:
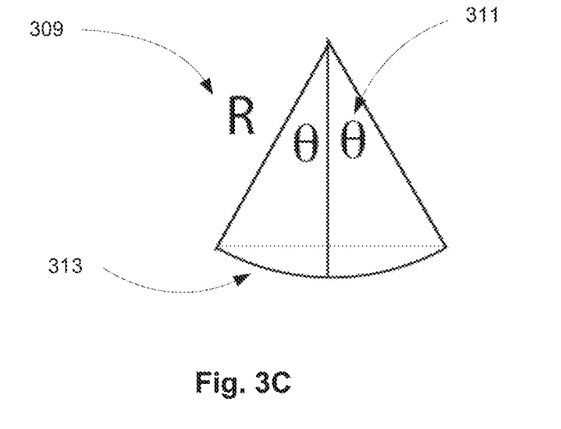

FIGS. 3A-3C are schematic diagrams illustrating exemplary non-planar chips based on slots according to embodiments described herein. For example, schematics 300A may include thin chips 305 of a thin die or wafer and exaggerated slot 301 with stress-relieve round corners at tip 307. When thin chips 305 is deformed, two sides of slot 301 may meet or close up. Thin chips 305 may be pre-stressed on a carrier substrate during fabrication process and become curved when released from the carrier substrate.

In one embodiment, thin chips 305 may comprise a circular chip with several radial slots (one or more) extending outward in the direction from the center of the circular chip (in a straight path or in a curved path, a spiral path, a zigzag path or other applicable paths) in fan/wedge shape with the surplus perimeters removed. The radial slots may extend from perimeter of thin chips 305 and stop at tips (e.g. fine tip about 1 μm in width) of the slots, such as tip 307 for slot 301, before (or at a distance from) reaching the center of thin chips 305. In one embodiment, tips of slots may be located within a thin chip to accommodate, for example, resolution limitation of micro fabrication process and/or increased stress intensity factors at the tip of the slot induced by chip deformation. Corners around tips of slots, such as around tip 307 of slot 301, may be rounded to reduce stress concentration associated with sharp corners and spread out stress over rounded slot corners when an associated chip is deformed or bended.

A slot may be formed by removing (or cutting, slitting), such as through deep reactive ion etching in the micro fabrication process, a portion of narrow channel area (e.g. a cutout, a longitudinal opening or narrow opening) of a chip, such as slot 301 of thin chips 305. The slot can reduce deformation stress, such as tangential in-plane stress, of the chip and increase allowable degrees of deformation of the chip. In one embodiment, the slot may break direct communication, within the chip, between circuit elements crossing the slots, thus jumpers (through the bonding pads to the constraining flex or another constraining chip, as will be described in the following), or longer power rails and data buses around the slots may be needed to distribute the power, ground & signal lines.

FIG. 3B shows a layered thin disk chip structure fabricated with slots and stressed films to bend or curve into a quasi-spherical patch and remain curved after release from a carrier wafer used during fabrication. Fixture structures may be bonded across the slots in the chip structure to prevent the curved chip from relaxing back to its original planar shape. The stress film may provide additional bending force to help constrain the chip to remain in a desired deformation. Although bending effect from stressed thin films on thin structures with one or more slots can greatly increase, large bending (e.g. 70-90 microns of edge displacement in the bending of a 30-micron thick retinal chip) may be associated with two dimensional constraints. Degrees of deformation may be measured, for example, in micros of edge displacement. As a result, relatively thicker films with large stresses (e.g. external bending) may be needed to achieve the desired large curvature.

FIG. 3C illustrates exemplary mechanisms to curve a planar chip. When a planar disk (e.g. including a planar chip) of diameter "d" is bent into a radius of curvature "R" 309, the angle 311 extended from the center of radius to the end points of a diameter line of the disk is $2\theta$, where $2R*\theta=d$. The original circumference of the disk is $S=\pi*d=2\pi R*\theta$; however, the deformed circumference 313 should be $S'=2\pi R*\sin(\theta)$ if the disk is deformed into a patch of a spherical shape. Since $\theta > \sin(\theta)$ when $\theta > 0$, the disk will experience in-plane tangential compressive stresses against the bending since there are excess of circumference $2\pi r*[\theta - \sin(\theta)]$ at a radius r less or equal R. The slots remove such excess in an appropriate amount such that the two edges of the slot is brought together when the disk is deformed into a spherical shape. This principle of removing certain excess material from a planar chip into a curved non-planar shape may be applicable in some embodiments described herein.

Figure 4A:
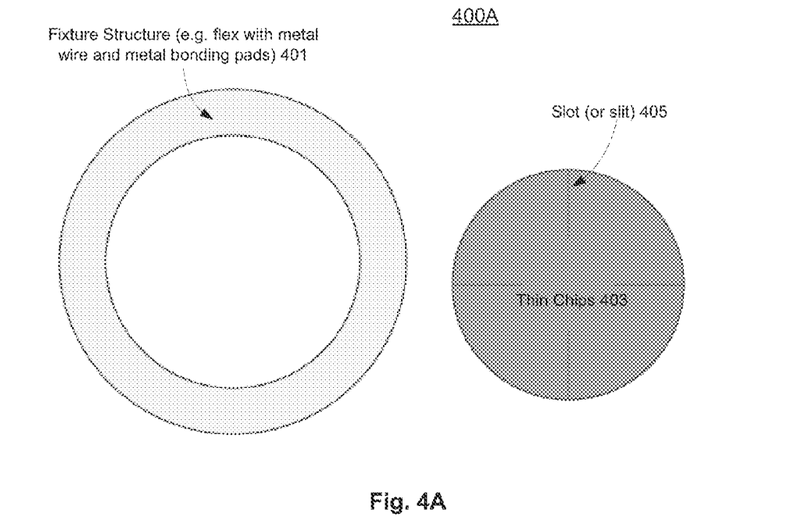
FIGS. 4A-4B are schematic diagrams illustrating exemplary embodiments of a thin chip assembled with a flex.
Figure 4B:
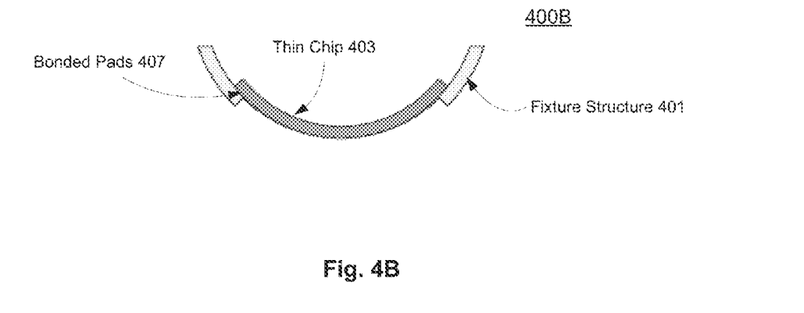

FIGS. 4A-4B are schematic diagrams illustrating exemplary embodiments of a thin chip assembled with a flex. Schematic 400A may include fixture structure 401 and thin chips 403. In one embodiment, fixture structure 401 may be a flex shaped in an annular ring (for example, formed from a flex "cable"). A flex may comprise a polymer (e.g. Polyamide) which can be transparent or translucent, deformable and/or moldable. In some embodiments, a flex may be shaped as a whole piece or in different applicable shapes according to desired deformation required. Thin chip 403 may be based on a thin wafer/die with slits for large deformation. In one embodiment, thin chips 403 may comprise flexible material with four slits (or slots), such as slot 405, to increase flexibility of the chip for large deformation. Fixture structure 401 may be bonded to flexible thin chip 403 to keep the chip in a bending state. The number and/or pattern of slots (e.g. 2, 12 or other applicable number of slots) formed on a thin chip may vary depending on desired deformation in the chip Turning now to FIG. 4B, assembly 400B may include curved thin chips 403 bonded with fixture structure 401 via, for example, bonded pads 407. Mechanical constraints from fixture structure 401 (or flex) may keep thin chips 403 to remain curved without relaxing back to its original flat state. Fixture structure 401 may include metal wires and metal bonding pads with appropriate thickness (for example, ~10 μm). Thin chips 403 may include matching (in relative location) bonding pads to be bonded with corresponding metal bonding pads of fixture structure 401. The metals may form thin-film bonding (for example, Au to Au) when under a pressure force in an elevated temperature (typically controlled within a range of 150 degree C. to 450 degree C.). The thin film bonding can also be used as electrical connections for data communication and power distribution.

FIGS. 5A-5F are block diagrams illustrating an exemplary sequence of assembly (or joining) process for a non-planar flexible device. For example, the non-planar flexible device may be fabricated or manufactured based on a curved thin wafer/die bonded with the flexible device via matching pads. At sequence 500A of FIG. 5A, in one embodiment, holder 501 may comprise a clear holder with recessed shapes, such as recess 503, to accommodate a flex or fixture structure. Recess 503 may accommodate flex material (e.g. polymer) which can be molded or shaped.

Figure 5A:
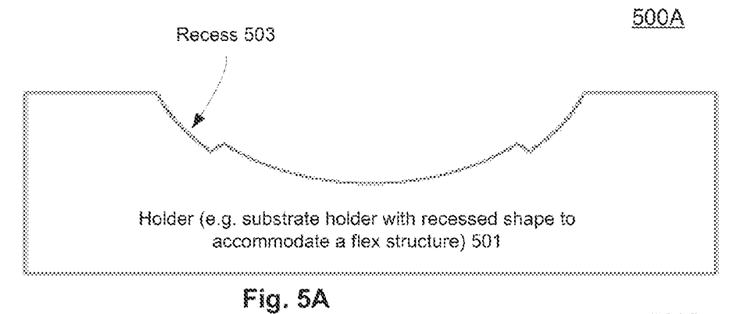
FIGS. 5A-5F are block diagrams illustrating an exemplary sequence of assembly process for a non-planar flexible device.
Figure 5B:
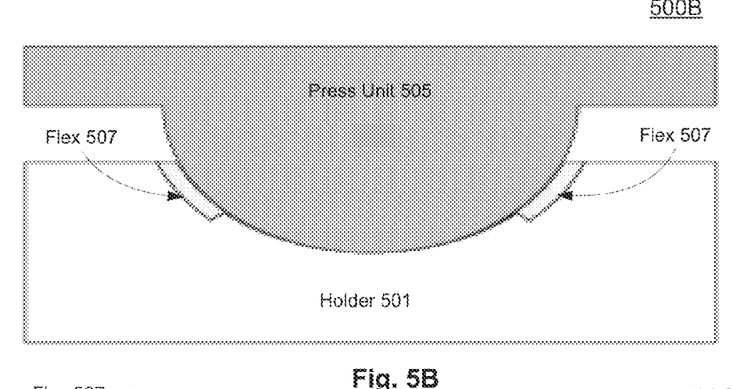
Figure 5C:
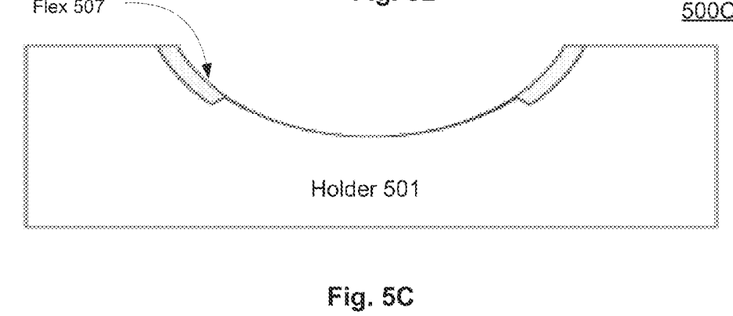

At sequence 500B of FIG. 5B, flex 507 may be tooled in recess 503. In one embodiment, press unit 505 and holder unit 501 may be brought together with pressure/heat applied to form flex 507 into a curved shape. Press unit 505 and holder unit 501 may be shaped with matching surfaces having a common or compatible radius of curvature. Flex 507 may be sandwiched between a press unit 505 (e.g. top unit) with spherical surface and holder unit 501 (e.g. bottom unit) with matching spherical recess. In one embodiment, flex 507 may comprise a polymer based ring held by vacuum (with vacuum holes on the surface of corresponding area, and vacuum channels inside holder 501) or by electrostatic force (e.g. using an electrostatic chuck). At sequence 500C of FIG. 5C, press unit 505 may be moved to separate from the holder unit 501 and leave flex 507 to remain deformed (or molded) in place (e.g. in recess 503). In some embodiments, thin chips bonded with a flex may be deformed based on mutual constraints between the flex and the thin chips without a need to mold the flex.

Figure 5D:
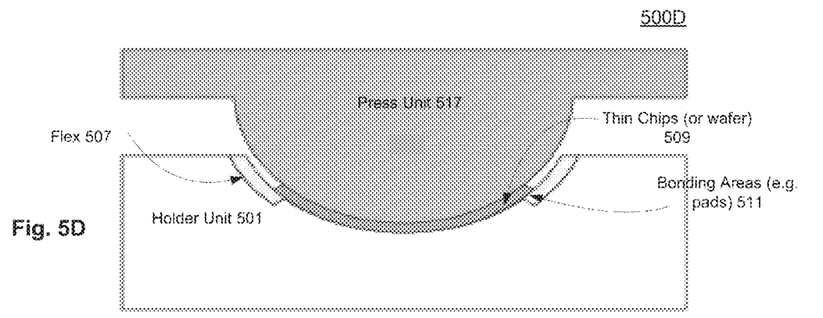
Figure 5E:
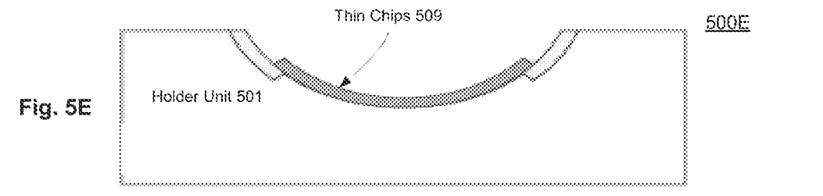

Turning now to FIG. 5D, at sequence 500D, press unit 505 and holder unit 501 may be brought together for bonding between thin chips (or wafer) 509 and flex 507 after press unit 517 and holder unit 501 are aligned. For example, thin chips 509 may be bonded or jointed with flex 507 at specific areas, such as bonding areas 511. Thin chip 509 may include metal based pads. Correspondingly, flex 507 may include matching pads. In one embodiment, press unit 505 may be aligned (e.g. via three dimensional rotational movements) with holder unit 501 to allow pads of thin chips 509 in contact with corresponding matching pads of flex 507. At least one of press unit 505 and holder unit 501 may be clear to allow the alignment. Press unit 505 of FIG. 5B and press unit 517 may be part of a plurality of press units with surfaces curved in different curvatures in one common assembly apparatus for non-planar devices.

In one embodiment, heat and pressure may be applied for bonding between thin chips 509 and flex 507, for example, to solder metal pads and corresponding matching pads together. Thin chips may be held on press unit (e.g. top press) 505, for example, via vacuum or electrostatics forces. Press 517 may be pressed against holder unit 501 after alignment of pads of thin chips 509 and matching pads of flex 507.

In some embodiments, flex 507 may be made through a clear bottom holder such as holder 501. Multiple layers of chips may be bonded via pressure and heat applied between a press unit and holder unit 501. Holder unit 501 may be associated with different shapes or styles of recesses to deform a flex or flexible chips, such as flex 507, depending on different chip designs. When the bonding is completed, at sequence 500E of FIG. 5E, press unit 505 may move away from holder unit 501 to release thin chip 509 bonded with flex 507 in a non-planar shape. Bonding pads may harden when cool down from bonding pressure/heat to cause separate chips/wafers to stick together (or bonded) in a curved or non-planar shape. In one embodiment, thin chips 509 bonded with flex 507 may be passivated (or coated) with barrier layers and/or polymer layers (e.g. to protect against corrosion) subsequent to sequence 5E. Air gaps between flex 507 (e.g. a separate chip mutually constrained to remain curved) and thin chips 509 may be backfilled with thermal conducting dielectric material for increase heat dissipation capability.

Figure 5F:
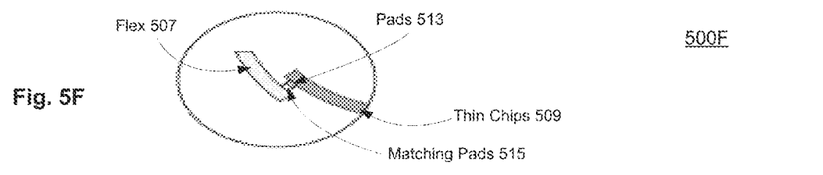

FIG. 5F shows an exaggerated view of a bonding pad between thin chips 509 and flex 507. For example, pad 513 of thin chips 509 may be bonded (or soldered) with matching pads 515 of flex 507. Pads 513 and matching pads 515 may comprise the same or different conducting material (e.g. gold). Bonding contact of a non-planar device, such as pads 513 bonded with matching pads 515, may be covered or coated (e.g. vapor coating or vacuum coating) with thin layer of hard passivation made of silicon nitride, diamond carbon or other applicable material to provide insulation and prevent exposing the bonding contact of the device. In one embodiment, bonding contacts may provide mechanical joining constraints and/or optional electrical connections between different portions of curved chips.

Figure 6A:
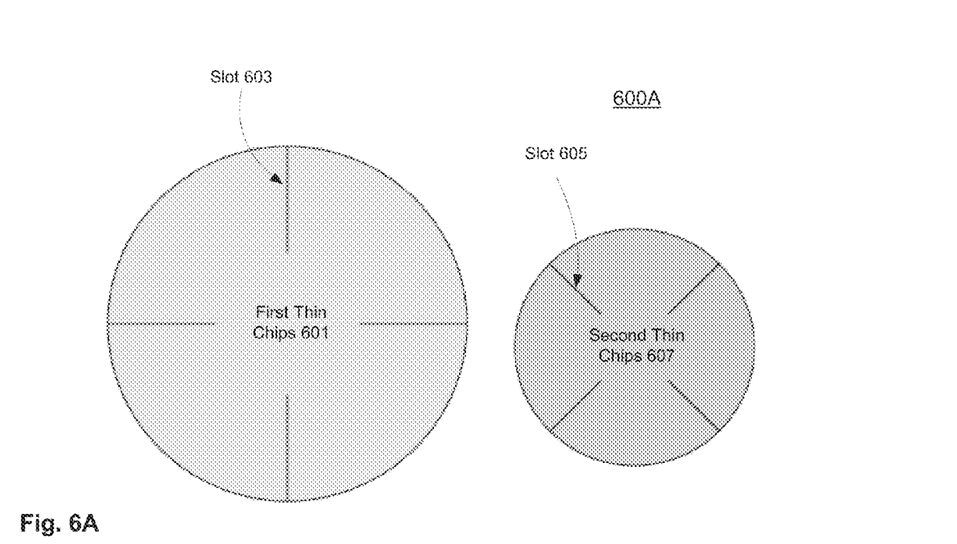
FIGS. 6A-6B are schematic diagrams illustrating exemplary embodiments of mutually constrained non-planar chips.
Figure 6B:
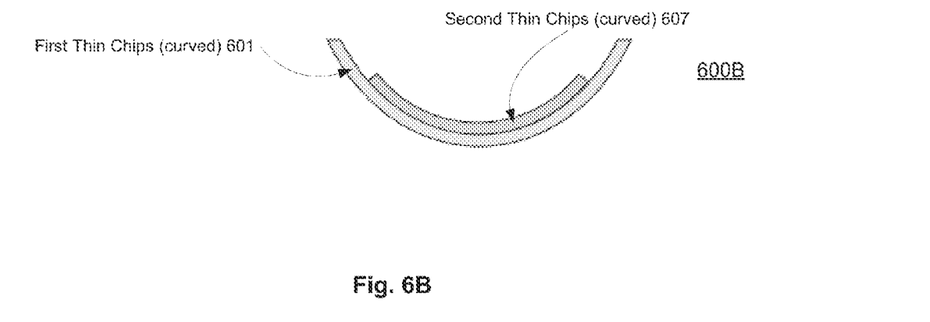

FIGS. 6A-6B are schematic diagrams illustrating exemplary embodiments of mutually constrained non-planar chips. For example, schematic 600A of FIG. 6A may illustrate two thin wafers/dies with off-set slits and matching bonding pads for mutual constraints for an assembly of curved chips. In one embodiment, first thin chips 601 and second thin chips 607 may each include four radial slots with matching metal bonding pads. Thin chips may be assembled with slots aligned with an angle. For example, slot 605 may cross slot 603 with a, for example, 45 degree angle in the assembled curved thin chips.

Turning now to FIG. 6B, assembly 600B may include first thin chips 601 and second thin chips 607 curved via mutual constraints. Assembled curved thin chips, such as first thin chip 601 and second thin chip 607, may not relax back to original flat or planar states because of mutual constraints applied to each other at bonding locations (e.g. bonding pad areas). In one embodiment, bonding pads may be paired across each slot of a thin chip to stick together portions of the chip across the slot.

Figure 7A:
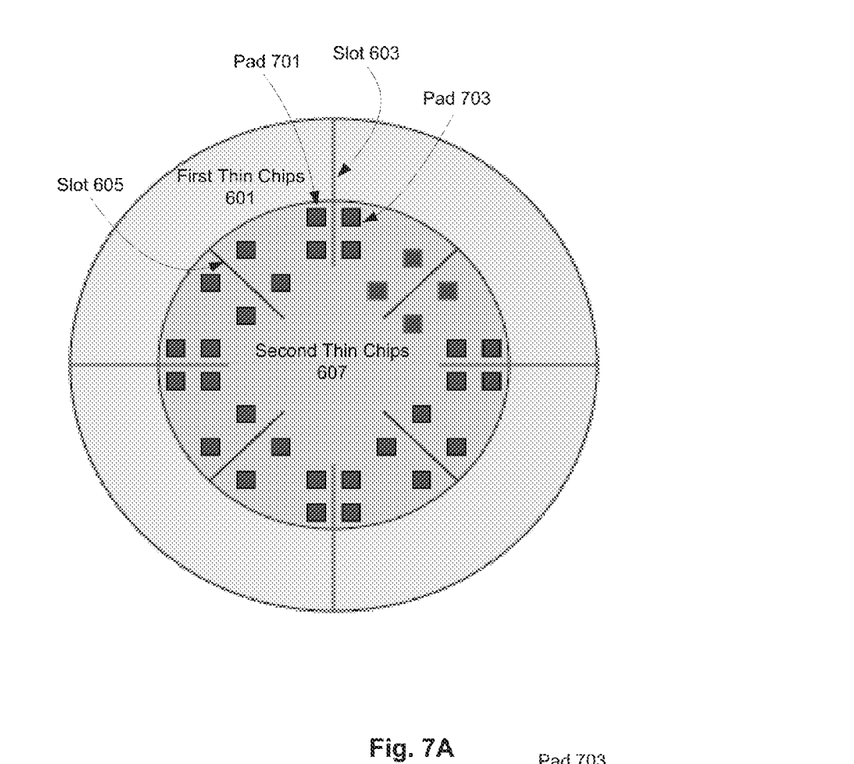
FIGS. 7A-7B are schematic diagrams illustrating exemplary top view and cross sectional view of an assembly with bonding pads.

FIGS. 7A-7B are schematic diagrams illustrating exemplary top view and cross sectional view of an assembly with bonding pads. For example, FIG. 7A illustrates a top view of a non-planar 3D packaging of a stack of two thin chips, such as second thin chips 607 over first thin chips 601, curved into quasi-spherical shape. Neighboring slots between the stacked chips may be aligned with an angle (e.g. 45 degrees), such as slot 605 of second thin chips 607 and slot 603 of first thin chips 601. The bonding pads may be positioned on both sides of slots, such as pads 701 and pads 703 across slot 603.

Figure 7B:
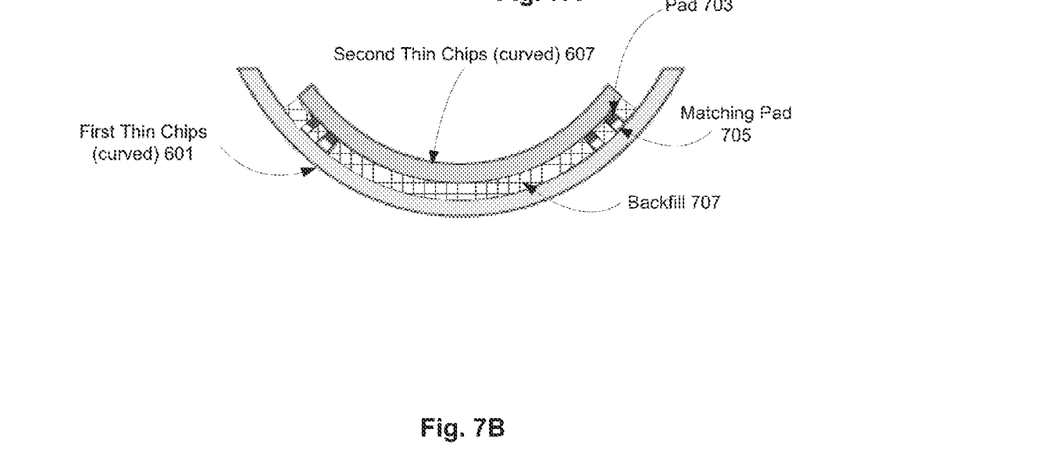

FIG. 7B illustrates a cross sectional view (e.g. not to scale with exaggeration) of the thin film bonding with bond pads regions. For example, second thin chips 607 and first thin chips 601 may remain curved via bonding of pads, such as bonding between pad 703 and matching pad 705. Alternatively or optionally, thin chips may be bonded via glue to remain in a non-planar shape.

In one embodiment, a backfill layer, such as backfill 707, between adjacent chips of a non-planar assembly stacking multiple chips may facilitate heat dissipation between the chips. A backfill layer may comprise thermal conductive dielectric material to control the temperature rise of the assembled structure (or non-planar chips) in operation. For example, heat generated from high speed processing circuitry embedded inside a non-planar assembly may be allowed to pass through both bonding pads and backfill layers to help cool down the non-planar assembly. In one embodiment, a backfill layer may reduce or eliminate thermal insulation of air gaps in a non-planner assembly. Alternatively, the non-planar assembly may be immersed in a liquid, such as silicon oil, to fill up air gaps to provide cooling effects.

The stack is not limited to two layers, or limited to round shapes. Multiple chips non-planar 3D stack with staggered slots can be formed. Power, signals and data can jump between layers to cross the slots to distribute electrical power and signals between stacked pieces and adjacent pieces. Since the active devices will be under bending stresses, the stress-induced effects such as the increase of trans-conductance for tensile stresses in both longitudinal and transverse directions on N-type MOS transistors, and either increase or decrease in the case of P-type transistors may be taken into account and pre-compensated in the system design.

Figure 8A:
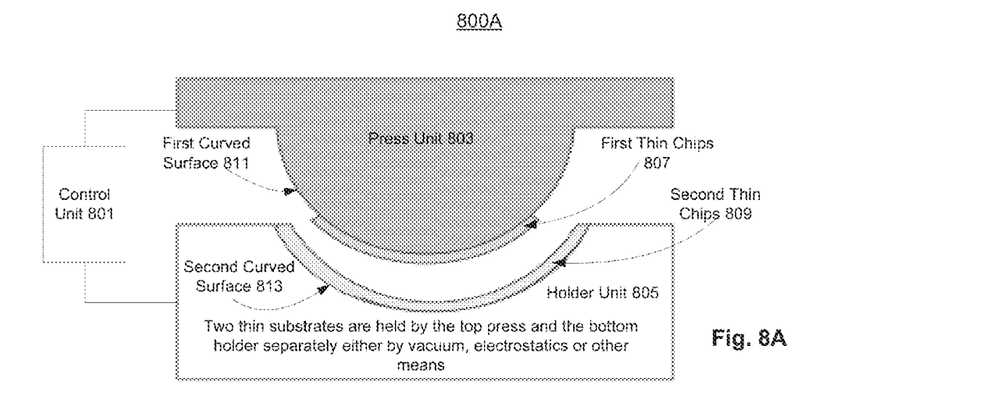
FIGS. 8A-8C are block diagrams illustrating an exemplary sequence to assemble curved stack of thin dies/wafers in one embodiment described herein.
Figure 8B:
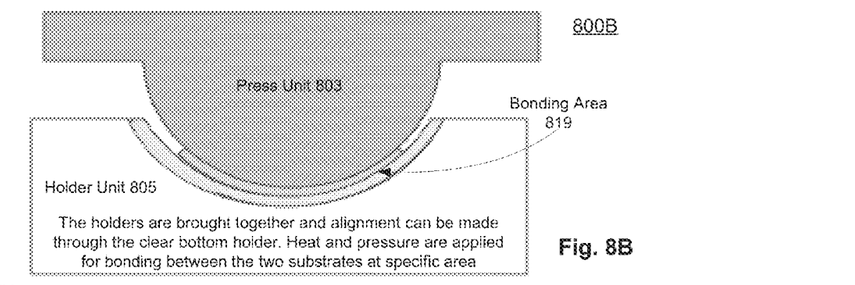
Figure 8C:
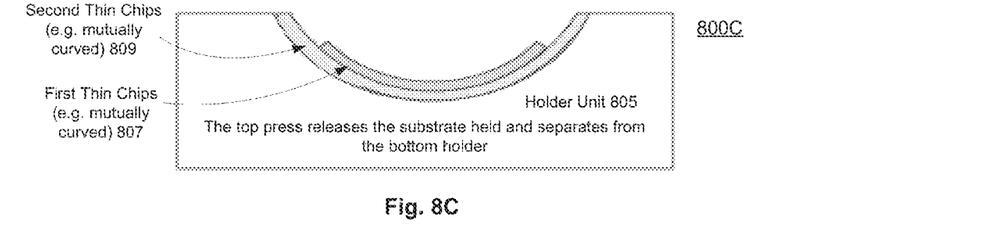

FIGS. 8A-8C are block diagrams illustrating an exemplary sequence to assemble curved stack of thin dies/wafers or substrates in one embodiment described herein. For example, at sequence 800A of FIG. 8A, two thin chips, first thin chips 807 and second thin chips 809, may be held in an assembly apparatus. In one embodiment, the assembly apparatus may include press unit 803 (e.g. upper unit), holder unit 805 (e.g. lower unit) and a control unit 801. Press unit 803 and/or holder unit 805 may move in a three dimensional manner including translational and/or rotational movements, for example, controlled by control unit 801.

In one embodiment, first thin chip 807 and second thin chip 809 may be separately held by press unit 803 and holder unit 805 either by vacuum, electrostatics or other means. For example, press unit 803 or holder unit 805 may comprise vacuum chucks with rings of small holes or openings of vacuum channels to provide suction forces to hold thin chips. Press unit 803 and holder unit 805 may be associated with matching surfaces to deform the thin chips held. In one embodiment, first thin chips 807, when held by press unit 803, may be deformed over first curved surface 811 of press unit 803. Second thin chips 809, when held by holder unit 805, may be deformed over second curved surface 813 of holder unit 805. First thin chips 807 and/or second thin chips 809 may include slots to increase flexibility of the chips to deform (or curve, bend). First curved surface 811 and second curved surface 813 may be of a common curvature to match each other.

At sequence 800B of FIG. 8B, holders may be brought together after alignment. For example, holder unit 805 may be clear or transparent to allow alignment with press unit 803 via first chin chips 807 and second thin chips 809. In one embodiment, alignment between holders may be based on matching corresponding bonding pads between first thin chips 807 and second thin chips 809 (e.g. based on masks).

Press unit 803 may rotate in three rotational dimensions for aligning chips held. In one embodiment, press unit 803 may be constrained to move in one translational dimension, for example, towards or away from holder unit 805, to allow surfaces of holders, e.g. first curved surface 811 and second curved surface 813, to match each other. In some embodiments, surfaces of the holders may match with a common center of curvature (or ball center).

As press unit 803 and holder unit 805 are brought together, heat and pressure may be applied for bonding between first thin chips 807 and second thin chips 809 at specific area of thin metal film bonding region, such as bonding area 819. Thin metal film bonding region may include pads aligned with matching pads between the thin chips. In one embodiment, pads may melt together using controlled ranges of elevated temperatures. For example, heat of about 100-180 degrees C. (Celsius) may be used for tin/lead based pads. Alternatively, heat of about 350-450 degrees C. may be needed for pads made of gold alloy.

At sequence 800C of FIG. 8C, press unit 803 may release first chips 807 held and separate itself from holder unit 805. A non-planar assembly including first chips 807 bonded with second chips 809 may remain curved via mutual constraints provided from established bonding between the chips.

In the foregoing specification, the invention has been described with reference to specific exemplary embodiments thereof. It will be evident that various modifications may be made thereto without departing from the broader scope of the invention as set forth in the following claims. The invention is not limited to the particular forms, drawings, scales, and detailed information disclosed. The specification and drawings are, accordingly, to be regarded in an illustrative sense rather than a restrictive sense.

What is claimed is:

1. An non-planar integrated circuit device, the device comprising:
   a flexible structure curved in a desired deformation from planar shapes, the flexible structure having a front surface, a back surface and a perimeter, the flexible structure including
   one or more layers of semiconductor material, the layers including a circuitry to perform processing operations, each layer being curved in the desired deformation;
   cutout channel openings arranged around a center portion of the flexible structure, wherein each cutout channel opening cuts through a thickness between the front surface and the back surface, the cut through of the thickness extending throughout the cutout channel opening longitudinally from the perimeter towards the center portion of the flexible structure, wherein the desired deformation from planar shapes causes displacement stresses in the flexible structure, the cutout channel openings to reduce the displacement stresses;
   a plurality of bonding structures extending externally over the layers of semiconductor material; and
   at least one fixture structure bonded to the flexible structure via the bonding structures to provide holding constraints allowing the flexible structure to remain curved.

2. The device of claim 1, wherein the fixture structures are curved according to the desired deformation and wherein the fixture structure bonded with the flexible structure to provide mutual holding constraints allowing the fixture structure to remain curved.

3. The device of claim 2, wherein the flexible structure includes a surface having a center, wherein the slots are arranged extending outwardly in a direction from the center of the surface, and wherein the curving is directed inwardly towards the center in a three dimensional manner.

4. The device of claim 3, wherein the desired deformation conforms substantially to a quasi-spherical shape.

5. The device of claim 3, wherein at least one of the fixture structures are bonded to the flexible structure across one of the slots via at least two of the bonding structures arranged within proximity of the one slot, and wherein the at least one fixture structure provides a portion of the holding constraints to keep openings of the one slot from being widened.

6. The device of claim 5, wherein the at least two of the bonding structures are positioned across two sides of the one slot.

7. The device of claim 5, wherein the one fixture structure comprises polymer material bended to a non-planar shape conforming the desired deformation for the flexible structure.

8. The device of claim 1, wherein the cutout channel openings form narrow openings as slots in the flexible structure, the slots to reduce in-plane stress of the flexible structures across the narrow openings to allow the curving in the desired deformation.

9. The device of claim 1, wherein the bonding structures include bonding pads comprising electrical conducting material, the fixture structure bonded with the flexible structure via the bonding pads.

10. The device of claim 9, wherein at least a portion of the flexible structure and the fixture structure are separated via backfill in the device, and wherein the backfill comprises thermal conducting material configured to dissipate heat between the flexible structure and the fixture structure.

11. The device of claim 9, wherein the bonding pads are passivated with at least one passivation layer to insulate the conducting material from corrosion.

12. The device of claim 11, wherein the device is configured to be implanted within a human eye to enable perception of a vision of light, wherein the desired deformation allows the implantation of the device to conform to a shape of a human eyeball.

13. The device of claim 12, wherein the flexible structure and the fixture structure are substantially transparent to allow light to pass through the device.

14. The device of claim 12, wherein the flexible structure includes an array of pixel units, wherein each pixel unit comprises a sensor to sense light, an electrode to deliver a stimulus to targeted neuron cells of the electrode for the perception, and processing circuitry to derive the stimulus from the light to drive the electrode.

15. The device of claim 9, wherein the fixture structure is configured to perform additional processing operations, and wherein the bonding pads enable communication between the flexible structure and the fixture structure with each other to coordinate between the processing operations and the additional processing operations.

16. The device of claim 15, wherein the communication includes relay of information across slots to the flexible structure via the fixture structure.

17. The device of claim 1, wherein the device has a three dimensional shape, wherein the desired deformation conforming to a portion of the three dimensional shape, the device further comprising:
at least one separate flexible structure configured for additional processing operations, wherein the separate flexible structure is curved conforming the three dimensional shape to allow a surface of the flexible structure and a separate surface of the separate flexible structure to face each other within the three dimension shape to enable the flexible structure and the separate flexible structure to directly communicate with each other across the surface and the separate surface within the device.

18. The device of claim 17, wherein the direct communication is performed wirelessly.

19. A three dimensional integrated circuit device having a three dimensional shaped surface, the device comprising:
a plurality of flexible chips, each flexible chip curved conforming to the three dimensional shaped surface, each chip including one or more layers of semiconductor material, the layers including circuitry to perform processing operations, each layer being curved conforming to the three dimensional shaped surface, wherein at least one of the flexible chips is configured with cutout channel openings arranged around a center portion of the at least one flexible chip, the at least one flexible chip having a front surface, a back surface and a perimeter, wherein each cutout channel opening cuts through a thickness between the front surface and the back surface, the cut through of the thickness extending throughout the cutout channel opening longitudinally from the perimeters towards the center portion of the at least one flexible structure, wherein the three dimensional shaped surface causes displacement stresses in the at least one flexible chip, the cutout channel openings to reduce the displacement stresses;
a plurality of bonding pads to bond the flexible chips, wherein each flexible chip is bonded with at least a separate one of the flexible chips via two or more of the bonding pads to provide mutual holding constraints to allow the bonded flexible chips to remain curved; and
connection paths between the at least two flexible chips to allow direct communication between the at least two flexible chips and wherein the bonding pads and the connection paths provide connection configuration among the chips enable the device to perform the processing operations.

20. The device of claim 19, wherein the at least two flexible chips are configured to face each other for establishing the connection paths.

21. The device of claim 19, wherein at least one of the chips include one or more slots to form narrow openings in the one chip to allow curving conforming to the three dimensional shape.

22. The device of claim 19, further comprising backfill material between the chips outside the bonding pads, the backfill material configured with thermal conducting to dissipate heat from the chips.

* * * * *